United States Patent [19]

Yano et al.

[11] 4,423,737
[45] Jan. 3, 1984

[54] COMBINATION TOMOGRAPHIC AND CARDIOGRAPHIC ULTRASONIC IMAGING METHOD AND SYSTEM

[75] Inventors: Tsutomu Yano, Kawasaki; Yoshihiro Hayakawa, Sagamihara; Ryobun Tachita, Kawasaki; Kazuyoshi Irioka, Sagamihara; Hiroshi Fukukita, Tokyo; Akira Fukumoto, Machida, all of Japan

[73] Assignee: Matsushita Electric Industrial Company, Limited, Osaka, Japan

[21] Appl. No.: 231,935

[22] Filed: Feb. 4, 1981

[30] Foreign Application Priority Data

Feb. 5, 1980 [JP] Japan ................................. 55-13166

[51] Int. Cl.³ ............................................. A61B 10/00
[52] U.S. Cl. .................................................... 128/661
[58] Field of Search ................ 128/660, 661, 662, 663

[56] References Cited

U.S. PATENT DOCUMENTS

| | | | |
|---|---|---|---|
| 3,954,098 | 5/1976 | Dick et al. ........................ | 128/660 |
| 4,267,584 | 5/1981 | McKeighen et al. ............... | 128/660 |
| 4,271,842 | 6/1981 | Specht et al. ...................... | 128/661 |
| 4,274,422 | 6/1981 | Anderson et al. ................. | 128/661 |
| 4,310,907 | 6/1982 | Tachita et al. ..................... | 128/660 |

OTHER PUBLICATIONS

Takemura et al., "Highspeed Ultrasono-Cardiotomograph," Sonolayergraph Model SSL51H.

*Primary Examiner*—Kyle L. Howell
*Assistant Examiner*—George Yanulis
*Attorney, Agent, or Firm*—Lowe, King, Price & Becker

[57] ABSTRACT

Ultrasonic echo signals are successively sampled and converted to digital echo data which are written into a first digital memory column by column and then read out row by row into a first buffer memory. The digital echo data which are derived in response to beams successively transmitted in a predetermined direction are written into columns of a second digital memory and read out of the memory in rows into a second buffer memory. The data stored in the first and second buffer memories are read out for digital-to-analog conversion and selectively applied within a television "frame" interval to control electron beam intensity of a single cathode ray tube so as to present tomographic and cardiographic images in different display areas of the tube.

9 Claims, 8 Drawing Figures

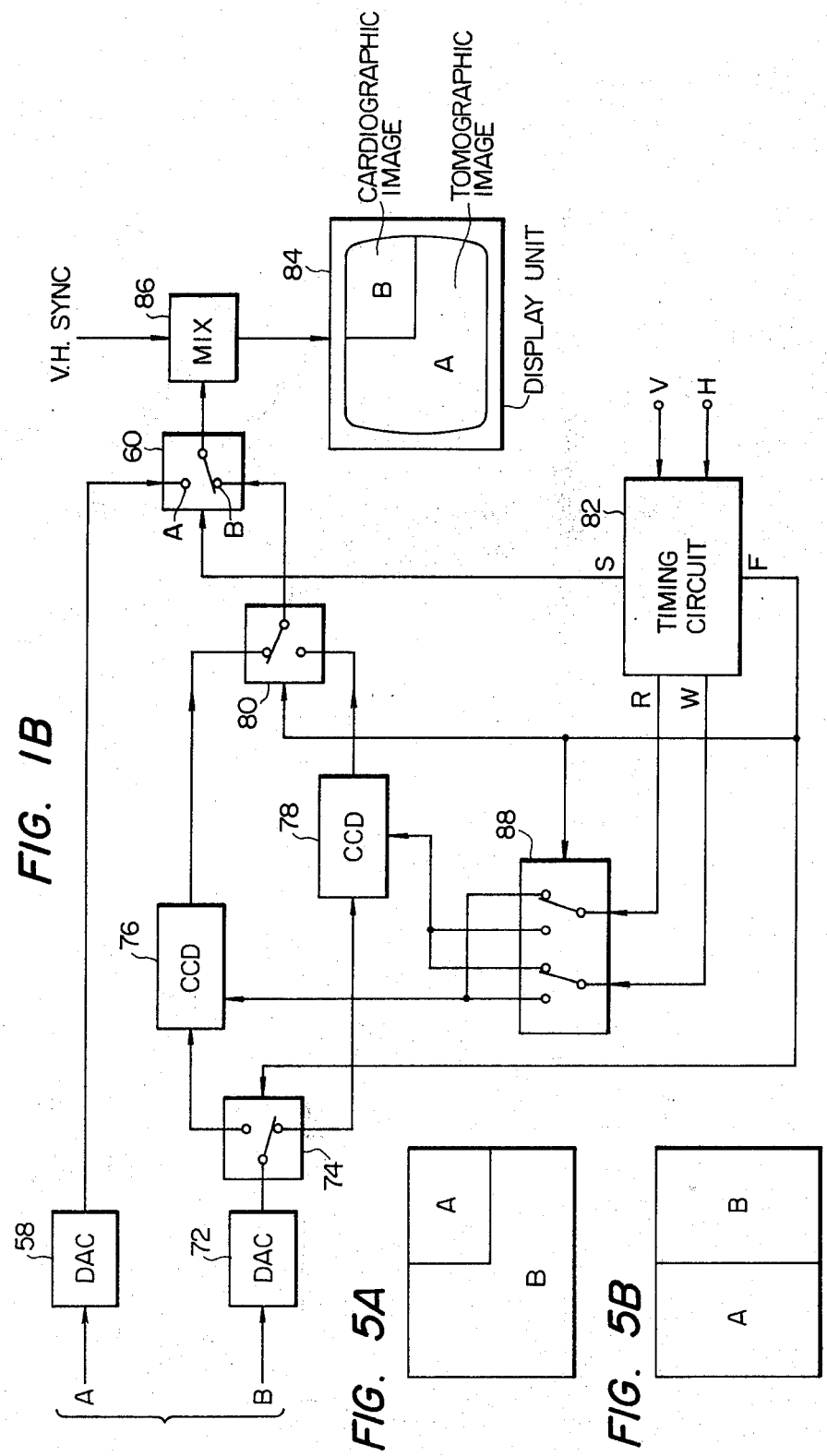

COMBINATION TOMOGRAPHIC AND CARDIOGRAPHIC ULTRASONIC IMAGING METHOD AND SYSTEM

BACKGROUND OF THE INVENTION

The present invention relates generally to ultrasonic imaging methods and systems, and in particular to a combination tomographic and cardiographic ultrasonic imaging system which presents the two different images simultaneously on a single cathode ray tube screen.

Presentation of ultrasound tomographic and cardiographic images conventionally involves the use of a common array of elemental transducers for transmission of an acoustic beam and reception of echo signals returning from different tissues of a human body. The acoustic beam used for tomographic representation is successively angulated at equal tangential increments to scan across a plane of the body, while the beam used for cardiographic representation is transmitted in a predetermined direction at different intervals from the intervals at which the tomographic representing beam is angulated. Because of the difference in the method of presenting the two ultrasound images, presentation of the two images currently requires two separate cathode ray tubes or involves the use of a single cathode ray tube on which the two images are selectively displayed. Either of these conventional methods is disadvantageous because it requires that these images be recorded on separate recording sheets for preservation.

SUMMARY OF THE INVENTION

The present invention provides an ultrasonic imaging method and system which allows tomographic and cardiographic images to be represented simultaneously on a single cathode ray tube of a television monitor to thereby permit the two ultrasound images to be recorded on a single recording sheet.

The ultrasonic imaging method and system of the invention comprise an ultrasonic beam scanner including an array of elemental transducers, first and second digital memories each having a matrix of cell locations, and a sampling and converting circuit which successively samples echo signals returning from interfaces between different tissues of the body and converts the echo samples to digital echo data. The digital echo data are written by columns or scan lines into the first digital memory, and read out of the memory by rows or raster lines, into a first buffer memory. The digital echo data which are derived in response to beams directed successively in a predetermined direction is written by columns (or scan lines) into the second digital memory and read out of the memory row by rows (or raster lines) into a second buffer memory. The data stored in the first and second buffer memories are read out for digital-to-analog conversion and applied selectively within a television "frame" interval to a single cathode ray display device to modulate the intensity of an electron beam scanned along television raster lines to simultaneously present tomographic and cardiographic images in different areas of the same viewing screen of the display device.

The ultrasonic imaging system of the invention is preferably of the sector scan type in which the ultrasound beam is successively angulated at equal tangential increments on either side of the normal to the common transducer array to present the tomographic image in a sector field configuration. This permits the cardiographic image to be presented in an area of the viewing screen adjacent to the origin point of the sector-scan steered ultrasound beams.

Interpolators are advantageously employed for generating additional data to supplement the data read out of the first and second digital memories. The original and interpolating data are written into first and second line memories and read out of these memories at appropriate constant rates for digital-to-analog conversion. The data stored in one of the first and second line memories is read out to be written into an analog memory at a rate higher than the rate at which the data is read out of the other line memory.

BRIEF DESCRIPTION OF THE DRAWINGS

The invention will be further described with reference to the accompanying drawings, in which:

FIGS. 1A and 1B are block diagrams of the sector-scan ultrasonic imaging system of the invention;

FIGS. 5A and 5B illustrate modifications of the invention in which tomographic and cardiographic images are presented in different areas of a viewing screen.

DETAILED DESCRIPTION

Figure 1A:
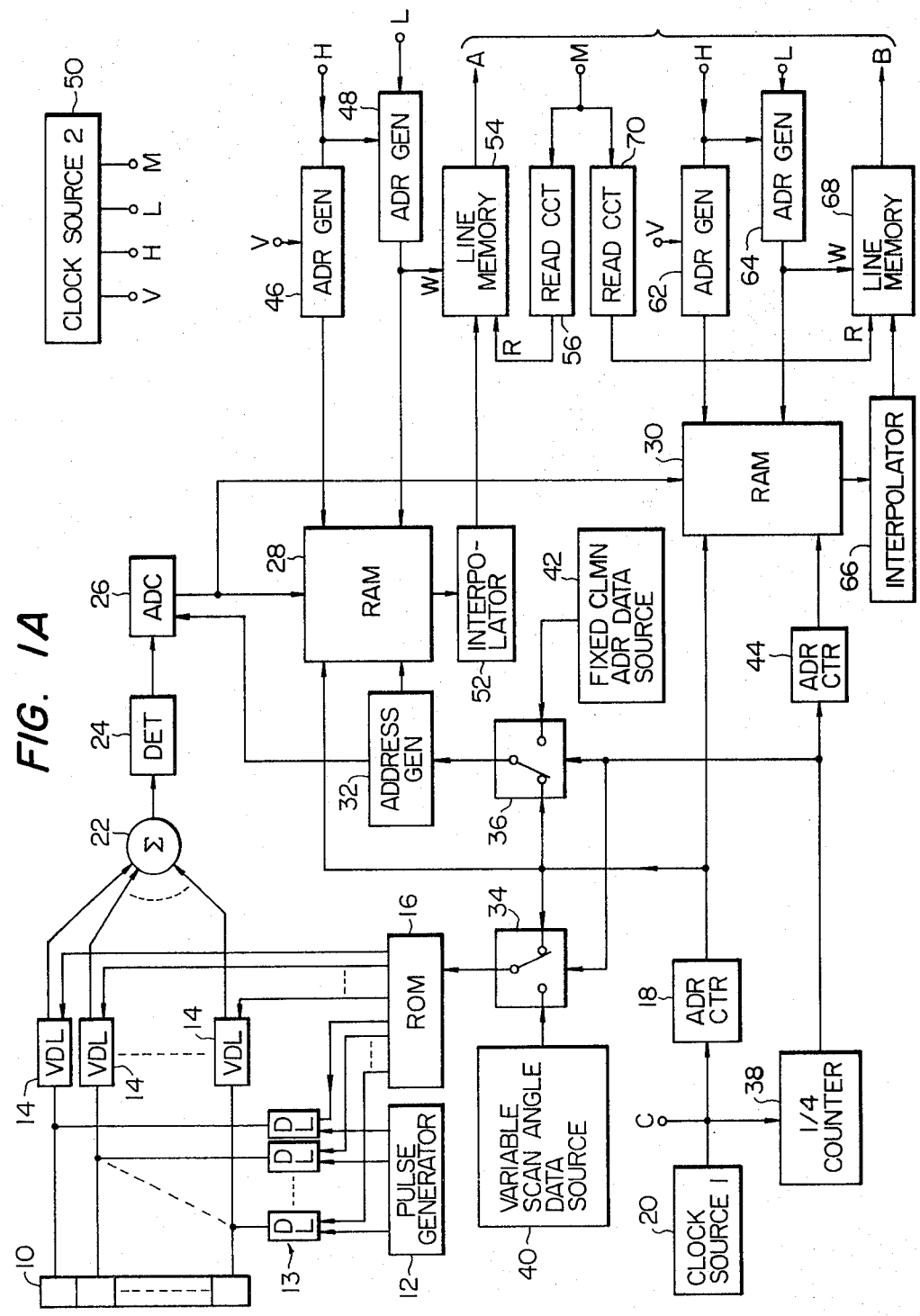
Figure 2:
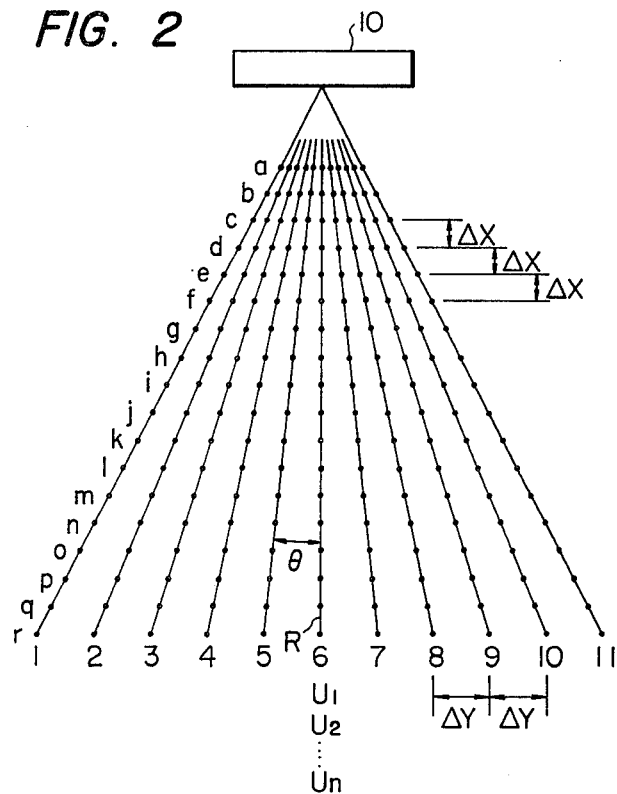
FIG. 2 is a view of the acoustic scan lines of the sector scanner on which data sample points, located on lateral raster lines are designated by letters

The ultrasonic tomographic and cardiographic imaging system of the invention, represented in FIGS. 1A and 1B, comprises a linear array 10 of piezoelectric transducer elements which are connected to a pulse generator 12 respectively via variable delay elements 13 for transmission of ultrasonic pulses. The ultrasonic pulses are delayed successively by delay data supplied from a read only memory (ROM) 16 to form a main ultrasonic beam. The amounts of the delay introduced to the delay elements 13 are varied successively so that the main beam is angulated at angles on either side of the normal to the transducer array 10 to create a sector scan field within a human body to be investigated to produce a tomographic image of a particular plane of the body. The main radial beam is deflected with a substantially equal tangential angular increment ΔY with respect to the normal or reference R as illustrated in FIG. 2.

The transmitted ultrasound energy is reflected from interfaces between different materials or tissues of the body with different amplitude and arrives at the transducers at successively delayed intervals prior to the transmission of a subsequent ultrasound beam. The received echo signals are applied respectively through variable delay elements 14 to a summing amplifier 22. The variable delay elements 14 are respectively supplied from the ROM 16 with delay data which cause the received signals to form a sharply focused point within the body. The delay data supplied to the variable delay elements 13 and 14 are generated in the ROM 16 in response to an address data from an address counter 18 at the clock rate of 3 kHz supplied from a first clock source 20. The echo signals are combined in the summing amplifier 22 and fed to a detector 24 where the high frequency components of the combined echo signal are eliminated to detect its envelope. The combined echo signal is then sampled at a rate which is inversely proportional to the cosine of angle $\theta$ of the radial main beam to the reference line R so that the sampled points in the sector scan format align themselves along television raster lines which are parallel to one another and to the transducer array 10 and spaced equally apart a distance $\Delta X$ as illustrated in FIG. 2. This sampling operation is accomplished by a sampling circuit formed by an analogdigital converter 26 and an address generator 32.

Figure 3A:
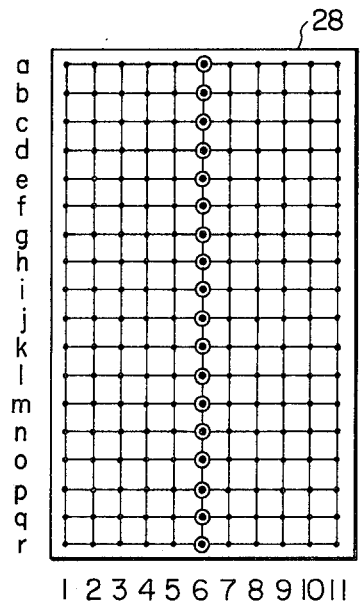
FIGS. 3A and 3B are schematic plan views of the arrangement of data stored in random access memories of the system for tomographic (dots) and cardiographic representations (circled dots), respectively.
Figure 4:
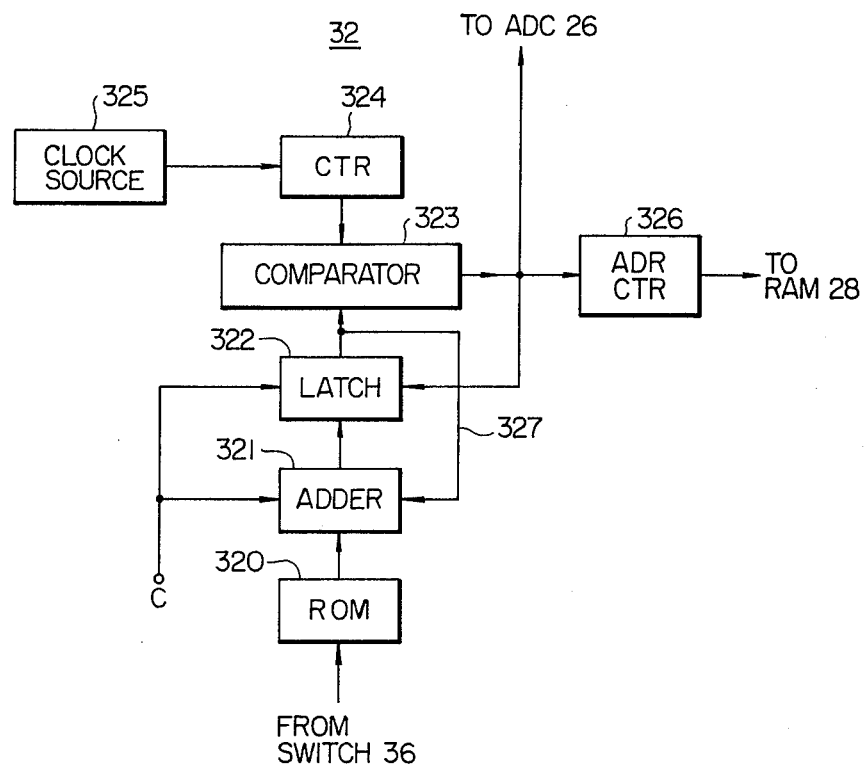
FIG. 4 is a block diagram of the detail of the address generator of FIG. 1A.

As shown in detail in FIG. 4, the address generator 32 comprises a read only memory 320, a digital adder 321, a latching circuit 322, a digital comparator 323, a binary counter 324, a clock source 325 which generates clock pulses at the frequency of 14 MHz, and an address counter 326. The ROM 320 is provided with a set of prerecorded sampling data, each data representing the incremental sampling interval for each of the radial scan beams #1 to #11, for example. This interval is inversely proportional to the cosine of the angle $\theta$ of the beam with respect to the normal R. Each sampling data is read out in response to an address data from the address counter 18 and supplied to a first binary data input of the adder 321. The contents of the adder 321 are transferred to the latch 322 as a reference data to the comparator 323 for making a comparison with another data supplied from the binary counter 324 which receives the 14 MHz clock pulse from the clock source 325. This binary counter 324 generates a binary representation of incremental data as a function of time at a rate of 1 bit in response to each input of the 14 MHz clock. When this time-varying binary data reaches the reference incremental sampling data stored in the latch 322, the comparator 323 generates a coincidence output and feeds it to the analog-digital converter 26 and to the latch 34 to cause the latter to transfer its contents to a second binary data input of the adder 321 through a feedback circuit 327 with the result that a predetermined amount of increment is accumulated twice in the adder 321 and transferred to the latch 322 and thence to the comparator 323. This process is repeated until all the sampling points a to r along a particular radial scan line are sampled. The latch 322 and adder 321 are cleared in response to the clock pulse supplied through a terminal C of the clock source 20 when the sampling operation is completed in regard to each beam deflection angle. In response to the next clock pulse of the clock source 20, a subsequent address data is retrieved from the ROM 320 and the above process is repeated to sample along the path of the next adjacent radial beam. The comparator 323 thus generates output pulses at intervals which are equally spaced apart as long as a particular beam path is sampled and varied inversely as a function of the cosine of the angle $\theta$ of the beam with respect to the normal R. The output of the comparator 323 is applied to the address counter 326 to generate an address data for each sampled point and supplies it to the RAM 28 together with the address data supplied from the counter 18 to write the echo data which is digitally converted in the converter 26 into the RAM 28 column by column so that the digital echo data are stored in an orthognal format as illustrated in FIG. 3A. The data stored in the RAM 28 is later used for generating a tomographic image.

According to the invention the address data from the address counter 18 is coupled via electronic switches 34 and 36 to the ROM 16 and address generator 32, respectively. The switches 34 and 36 are activated in response to a control signal supplied from a divide-by-4 counter 38 upon receipt of every four clock pulses from the clock source 20 to generate an ultrasonic beam for purposes of generating a cardiographic image. When the switches 34 and 36 are activated, the ROM 16 is supplied with a manually adjustable scan angle data from a source 40 to cause the transmitted ultrasound beam to be deflected to a predetermined angle, preferably coinciding with the normal R. This ultrasound beam for the cardiographic purpose may be angulated to any desired direction by a manual adjustment of the data source 40. The address generator 32 is supplied with a fixed column address data from a data source 42 to sample the points transmitted in parallel with the scan beam along the normal R and write the corresponding digital echo data along #6 column as marked in circled dots in FIG. 3A.

Figure 3B:
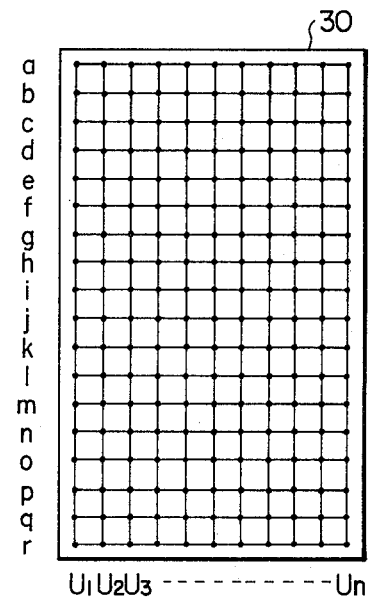

This cardiographic digital echo data is also supplied to the RAM 30 and writen thereinto by address data from an address counter 44 which receives its input from the output of the divide-by-4 counter 38 and by the address data from the counter 18 so that the input data are stored column by column as in RAM 28 into a format as illustrated in FIG. 3B in which $U_1$, $U_2$ to $U_n$ represent the ultrasound cardiographic (UCG) pulse beams successively transmitted along the reference line R at every four radial scan intervals (see also FIG. 2).

The data stored in the RAM 28 are retrieved row by row in response to a row address data supplied from an address generator 46 and column address data from an address generator 48. The address generator 46 is in receipt of horizontal sync pulses H supplied from a clock source 50 when enabled by a vertical sync pulse V also supplied from the clock source 50 so that each row address data is generated in synchronism with each horizontal scan line. The address generator 48 is enabled in response to the horizontal sync pulse to generate each column address data in response to clock pulses L which occur in the clock source 50 at (1/N)th intervals of the horizontal scan period, where N represents the total number of radial scan beams of the sector field. Each row data from the RAM 28 are fed into an interporator 52 in which additional digital echo data are synthesized by the technique of interporation. The original and interpolating data are successively supplied to a line memory unit 54 in response to the output of the address generator 48. The data stored in the line memory unit 54 are read out in response to an address data generated by a reading circuit 56 in response to clock pulses M supplied from the clock source 50. The clock pulses M occur at a rate much higher than the frequency of the clock pulses L, typically 14 MHz. The details of the interporator 52, line memory unit 54 and the reading circuit 56 are shown and described in U.S. Pat. No. 4,310,907 which is assigned to the same assignee of the present application. As described in this patent, the use of the interporator permits the echo data to be displayed in an orthognal array rather than in a radial array in which undesired Moire fringe patterns are likely to occur and also permits the ROM's 28 and 30 and the associated line memories to be addressed for reading at constant rates.

The echo data retrieved from the line memory 54 are applied as a sector scan field signal A to a digital-analog converter 58 (FIG. 1B) to recover the original echo amplitude signal which is applied to an input terminal of switch 60.

The UCG data now stored in the RAM 30, on the other hand, are retrieved row by row in response to row address data supplied from an address generator 62 and in response to column address data from an address generator 64. The address generator 62 receives the horizontal sync pulses H to generate each address data in synchronism with each horizontal scan line when enabled by a vertical sync pulse V. The address generator 64 is supplied with the clock pulse L to generate as many column address data as is necessary for cardiographic representation when enabled by a horizontal sync pulse H. Identically to the RAM 28, the retrieved UCG row data from the RAM 30 are fed to an interpolator 66 of substantially identical construction to the interpolator 52. Thus, the UCG row data are interpolated in a similar manner to that described above and fed into a line memory unit 68 in response to the output of the address generator 64. The UCG data stored in the line memory unit 68 are read out in response to an address signal from a reading circuit 70 similar in construction to the reading circuit 56 and supplied as a display data B to a digital-analog converter 72 and thence to the input of a switch 74. The switch 74 selectively couples the input analog UCG signal to one of its outputs and thence to a charge coupled device 76 or 78. The outputs of the charge coupled devices 76 and 78 are connected to respective inputs of a switch 80. The switches 74 and 80 are controlled in response to a "field" enable signal F which is generated by a timing circuit 82 when a given "field" of interlaced lines is displayed on a cathode-ray display unit 84 so that the moving contact arm of each switch is connected alternately to the charge coupled devices 76 and 78 with the contact arm of the other switch, whereby when one charge coupled device is being supplied with input data during the first field interval the other device is delivering its output to the switch 60 and thence to a mixer 86, and during the second field interval the situation is reversed.

The charge coupled devices 76 and 78 are respectively operated by write and read clock signals supplied from the timing circuit 82 through a switching unit 88 to provide writing and reading operations in synchronism with the field enable signal. More specifically, when the field enable signal F is applied to the switch 88, the writing clock signal is applied to the CCD 76 to store the UCG data of a field scan and the reading clock signal is applied to the CCD 78 to retrieve the UCG data therefrom and in the absence of the field enable signal F, the operating modes of the CCD's 76 and 78 are reversed.

Each of the CCD's 76, 78 is read out at a rate twice the rate at which the sector scan data is retrieved from the line memory unit 54. During the first half period of each of the horizontal scan lines that exist in the first half of the vertical scan period, the switch 60 is held in the A position to supply the sector scan data A to the mixer 86 and during the second half period of the same horizontal scan lines, the switch 60 is switched to the B position to supply the UCG data to the mixer 86. This is accomplished by a selection pulse S supplied from the timing circuit 82. During the remainder line scans that exist in the second half of the vertical period, the switch 60 is held in the A position to supply the sector scan data to the mixer 86. The mixer 86 is also supplied with vertical sync pulses V and horizontal sync pulses H to generate a composite video signal which is applied to the display unit 84 to intensity modulate the electron beam of the display cathode ray tube, so that a time-motion representation of the cardiac structure along the radial line path which is manually selected according to the data supplied from the variable scan angle data source 40 is produced in the upper right corner of the display screen as indicated by B simultaneously with a sector scan tomographic picture produced in the remainder area of the screen as indicated by A.

It is seen from the above description that the sector scan ultrasound image can alternatively be produced in the upper right corner of the screen while the cardiographic image is produced in the remainder part as shown in FIG. 5A by reversing the connections between the outputs of line memories 54 and 68 and the digital-analog converters 58 and 72. The timing circuit 82 is modified obviously so that the tomographic image and the cardiographic image are produced in the left and right halves of the full screen area as illustrated in FIG. 5B.

What is claimed is:

1. An ultrasonic imaging system for diagnostic purposes comprising:
   first means including an array of transducer elements for successively transmitting ultrasonic energy along each of a plurality of successive line paths to scan across the body of a patient;
   second means for sampling and converting ultrasonic echo signals representative of the amplitude of ultrasonic energy returning along said scan paths to digital echo data;
   first and second digital memories each having a matrix of storage cell locations arranged in columns and rows;
   third means for writing the digital echo data into columns of said first memory for storage and for reading out the stored echo data by rows into a first digital-to-analog converter to generate a first signal corresponding to a tomographic representation of the scanned cross-section of said body;
   fourth means for writing said digital echo data generated in response to the ultrasonic echo signals successively returning along a desired line path into columns of said second memory for storage and for reading out the stored echo data by rows into a second digital-to-analog converter to generate a second signal corresponding to a time-motion representation of the cardiac structure along said desired line path; and
   fifth means responsive to said first and second signals for providing a simultaneous display of said tomographic and time-motion representations in respective different areas of a single viewing screen.

2. An ultrasonic imaging system as claimed in claim 1, wherein said first means comprises means for transmitting ultrasonic energy along each of said plurality of successive line paths at first equal intervals to generate said digital echo data written into said first memory and for transmitting ultrasonic energy along said desired line path successively at second equal intervals to generate said digital echo data written into said second memory, said second equal intervals being greater than said first equal intervals.

3. An ultrasonic imaging system as claimed in claim 1 or 2, wherein said first means comprises means for transmitting said ultrasonic energy along each of a plurality of line paths successively angulated at equal tangent increments, and wherein said second means comprises means for sampling and converting said ultrasonic echo signals at rates which vary inversely with the cosine of the angle of the line paths, whereby the points at which said echo signals are sampled are aligned into lateral raster lines perpendicular to the normal to said transducer array.

4. An ultrasonic imaging system as claimed in claim 1 or 2, wherein said fifth means comprises an analog memory, two-dimensional display means having said viewing screen, means for writing one of said first and second signals into said analog memory and reading the stored signal into said display means at intervals, and means for applying the other of said first and second signals to said display means at alternate intervals with said signal read out of said analog memory.

5. An ultrasonic imaging system as claimed in claim 4 wherein said analog memory comprises a charge coupled device.

6. An ultrasonic imaging system as claimed in claim 1 further comprising a first interportator connected to receive data read out of said first digital memory before being applied to said first digital-to-analog converter for writing interpolating data in addition to said data read out of the first digital memory into a first line memory and reading the stored data out of the first line memory at a constant rate into said first digital-to-analog converter.

7. An ultrasonic imaging system as claimed in claim 6, further comprising a second interpolator connected to receive data read out of said second digital memory before being applied to said second digital-to-analog converter for writing interpolating data in addition to said data read out of the second digital memory into a second line memory and reading the stored data output of the second line memory at a constant rate into said second digital-to-analog converter.

8. An ultrasonic imaging system as claimed in claim 1, wherein said fourth means further comprises means for manually selecting a desired line path and causing said ultrasonic energy to be transmitted along the selected line path.

9. An ultrasonic imaging method using an array of transducer elements for transmitting ultrasonic energy, memory circuitry for storing data and a single viewing screen, comprising the steps of scanning the body of a patient by successively transmitting ultrasonic energy from the transducer elements across each of a plurality of successive line paths across the body; sampling and converting ultrasonic and echo signals representative of the amplitude of ultrasonic energy returning along the scan paths to digital echo data; storing the digital echo data into columns of a first memory and reading out the stored echo data by rows; converting the read out stored echo data into an analog first signal corresponding to a tomographic representation of the scanned cross-section of the body; storing the digital echo data generated in response to the ultrasonic echo signals successively returning along a desired line path into columns of a second memory and reading out the stored echo data by rows; converting the last mentioned read out data to a second analog signal corresponding to a time-motion representation of the cardiac structure along the desired line path; and responding to the first and second signals to provide a simultaneous display of the tomographic and time-motion representations in respective different areas of the screen.

* * * * *